US012178387B2

(12) United States Patent
McDowall et al.

(10) Patent No.: US 12,178,387 B2
(45) Date of Patent: Dec. 31, 2024

(54) AUGMENTED MEDICAL VISION SYSTEMS AND METHODS

(71) Applicant: Intuitive Surgical Operations, Inc., Sunnyvale, CA (US)

(72) Inventors: Ian E. McDowall, Woodside, CA (US); Alexander L Antaris, Emerald Hills, CA (US); Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 665 days.

(21) Appl. No.: 17/424,113

(22) PCT Filed: Jan. 22, 2020

(86) PCT No.: PCT/US2020/014526
§ 371 (c)(1),
(2) Date: Jul. 19, 2021

(87) PCT Pub. No.: WO2020/154351
PCT Pub. Date: Jul. 30, 2020

(65) Prior Publication Data
US 2022/0095903 A1 Mar. 31, 2022

Related U.S. Application Data

(60) Provisional application No. 62/797,186, filed on Jan. 25, 2019.

(51) Int. Cl.
*A61B 1/00* (2006.01)
*A61B 1/04* (2006.01)
*A61B 1/06* (2006.01)

(52) U.S. Cl.
CPC ...... *A61B 1/000094* (2022.02); *A61B 1/0005* (2013.01); *A61B 1/043* (2013.01); *A61B 1/0638* (2013.01)

(58) Field of Classification Search
CPC ........ A61B 1/00009; A61B 2034/2055; A61B 2090/365; A61B 34/20; A61B 34/25;
(Continued)

(56) References Cited

U.S. PATENT DOCUMENTS 9,211,058 B2 * 12/2015 McDowall ........... A61B 5/0071
9,668,820 B2 * 6/2017 Neubauer .............. A61B 90/98
(Continued)

FOREIGN PATENT DOCUMENTS

| EP | 2366327 A2 | 9/2011 |
| EP | 2394565 A1 | 12/2011 |
| EP | 2629504 A1 | 8/2013 |

OTHER PUBLICATIONS

International Search Report and Written Opinion for Application No. PCT/US2020/014526, mailed Jun. 24, 2020, 10 pages.
(Continued)

*Primary Examiner* — Peter D Le

(57) ABSTRACT

A system directs an imaging device to continuously capture visible light and fluorescence illumination from a surgical area. The system generates a visible light image stream based on the captured visible light and a fluorescence image stream based on the captured fluorescence illumination. The system operates in a first display mode by directing a display device to display a first video stream based on a first set of at least one of the visible light image stream and the fluorescence image stream. In response to detecting an event that occurs within the surgical area, the system switches from operating in the first display mode to operating in a second display mode by directing the display device to display a second video stream based on a second set of at least one of the visible light image stream and the fluorescence image stream, the first Instructions set being different than the second set.

18 Claims, 12 Drawing Sheets

(58) Field of Classification Search
CPC . A61B 5/0066; A61B 5/02014; A61B 5/0215;
A61B 5/743; A61B 90/361; A61B 90/37;
G06F 3/012; G06T 11/60; G06T
2207/30021; G06T 7/70
See application file for complete search history.

(56) References Cited

U.S. PATENT DOCUMENTS

| | | | | |
|---|---|---|---|---|
| 2004/0109231 | A1* | 6/2004 | Haisch | G01N 21/6428 |
| | | | | 359/385 |
| 2005/0059894 | A1* | 3/2005 | Zeng | A61B 1/043 |
| | | | | 600/476 |
| 2008/0111894 | A1* | 5/2008 | Tanimoto | H04N 23/843 |
| | | | | 348/222.1 |
| 2009/0192349 | A1* | 7/2009 | Berguer | A61B 1/043 |
| | | | | 600/109 |
| 2010/0164950 | A1* | 7/2010 | Zhao | A61B 34/20 |
| | | | | 345/419 |
| 2011/0046476 | A1* | 2/2011 | Cinquin | G09B 23/285 |
| | | | | 600/424 |
| 2011/0082369 | A1* | 4/2011 | Mohr | A61B 1/043 |
| | | | | 600/431 |
| 2011/0152692 | A1* | 6/2011 | Nie | A61B 5/7425 |
| | | | | 600/473 |
| 2012/0002012 | A1* | 1/2012 | O'Grady | H04N 13/239 |
| | | | | 348/E13.001 |
| 2012/0092488 | A1* | 4/2012 | Delaney | G01B 11/0608 |
| | | | | 348/128 |
| 2013/0274596 | A1* | 10/2013 | Azizian | A61B 34/30 |
| | | | | 600/424 |
| 2014/0296718 | A1* | 10/2014 | Kishima | G06T 7/30 |
| | | | | 382/128 |
| 2015/0181153 | A1* | 6/2015 | Mima | H04N 23/63 |
| | | | | 348/333.1 |
| 2016/0062103 | A1* | 3/2016 | Yang | A61B 1/07 |
| | | | | 250/552 |
| 2016/0317003 | A1* | 11/2016 | Ogata | G02B 23/2461 |
| 2017/0128152 | A1* | 5/2017 | McDowall | G03B 15/03 |
| 2017/0273707 | A1* | 9/2017 | Sakamoto | A61B 1/0638 |
| 2018/0153408 | A1* | 6/2018 | Yao | A61B 5/0075 |
| 2018/0228555 | A1 | 8/2018 | Charron et al. | |
| 2019/0059736 | A1* | 2/2019 | Maier-Hein | A61M 5/19 |
| 2019/0254759 | A1* | 8/2019 | Azizian | A61B 34/30 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2020/014526, mailed on Aug. 5, 2021, 8 pages.

* cited by examiner

| Event | Instrument Type | Current Mode | User ID | Display Mode |
|---|---|---|---|---|
| movement | graspers | visible_light | | augmented |
| movement | cautery_hook | fluorescence | | visible_light |
| energization | any | any | | visible_light |
| operation | scissors | fluorescence | user_A | visible_light |
| operation | scissors | fluorescence | user_B | augmented |
| idle_state | graspers | visible_light | user_A | augmented |
| idle_state | needle_driver | augmented | user_A | fluorescence |

Fig. 9

AUGMENTED MEDICAL VISION SYSTEMS AND METHODS

RELATED APPLICATIONS

The present application is a U.S. National Stage Application under 35 U.S.C. § 371 of International Application No. PCT/US2020/014526, filed on Jan. 22, 2020, which claims priority to U.S. Provisional Patent Application No. 62/797,186, filed on Jan. 25, 2019, and entitled "AUGMENTED MEDICAL VISION SYSTEMS AND METHODS," the contents of which are hereby incorporated by reference in their entirety.

BACKGROUND INFORMATION

An imaging device (e.g., an endoscope) may be used during a surgical procedure to capture images of a surgical area associated with a patient. The images may be presented (e.g., in the form of a video stream) to a surgeon during the surgical procedure to assist the surgeon in performing the surgical procedure.

In some examples, the images of the surgical area may include or be augmented with other imagery, such as fluorescence imagery based on detected infrared radiation (e.g., near-infrared radiation, short-wavelength infrared radiation, and/or long-wave infrared radiation) and/or other imagery generated based on techniques such as optical coherence tomography, to highlight certain portions of the surgical area (e.g., certain tissue types, anatomical landmarks, organs, blood vessels, certain disease states such as cancer or ischemia, etc.) in a selected color (e.g., green). During a surgical procedure, the surgeon may manually switch (e.g., by pressing a button, giving a voice command, or providing other user input) between a non-augmented display mode (e.g., a "normal" mode in which images of the surgical area, as captured under visible light, are displayed without being augmented by fluorescence imagery or other imagery) and an augmented display mode (e.g., a mode in which images of the surgical area are displayed while being augmented by fluorescence imagery or other imagery) in order to see desired image content that may help with the surgical procedure. However, manually switching between display modes can be distracting to the surgeon and may not always be performed by the surgeon at appropriate or relevant times during the surgical procedure.

SUMMARY

An exemplary system may comprise a memory storing instructions and a processor communicatively coupled to the memory and configured to execute the instructions to direct an imaging device to continuously capture visible light and fluorescence illumination from a surgical area; generate a visible light image stream based on the captured visible light and a fluorescence image stream based on the captured fluorescence illumination; operate in a first display mode by directing a display device to display a first video stream based on a first set of at least one of the visible light image stream and the fluorescence image stream; detect, while operating in the first display mode, an event that occurs within the surgical area; and switch, in response to the detection of the event, from operating in the first display mode to operating in a second display mode, wherein the operating in the second display mode comprises directing the display device to display, in place of the first video stream, a second video stream based on a second set of at least one of the visible light image stream and the fluorescence image stream, the first set being different than the second set.

An exemplary system may comprise a memory storing instructions and a processor communicatively coupled to the memory and configured to execute the instructions to direct an imaging device to continuously capture visible light and fluorescence illumination from a surgical area; generate a visible light image stream based on the captured visible light and a fluorescence image stream based on the captured fluorescence illumination; direct a display device to display only the visible light image stream; detect, while the visible light image stream is displayed, an event that occurs within the surgical area; and switch, in response to the detection of the event, from directing the display device to display only the visible light image stream to directing the display device to display another video stream based at least in part on the fluorescence image stream.

An exemplary method may comprise directing, by an augmented medical vision system, an imaging device to continuously capture visible light and non-visible light from a surgical area; generating, by the augmented medical vision system, a visible light image stream based on the captured visible light and a non-visible light image stream based on the captured non-visible light; operating, by the augmented medical vision system, in a first display mode by directing a display device communicatively coupled with the augmented medical vision system to display a first video stream based on a first set of at least one of the visible light image stream and the non-visible light image stream; detecting, by the augmented medical vision system while operating in the first display mode, an event that occurs within the surgical area; and switching, by the augmented medical vision system in response to the detection of the event, from operating in the first display mode to operating in a second display mode, wherein the operating in the second display mode comprises directing the display device to display, in place of the first video stream, a second video stream based on a second set of at least one of the visible light image stream and the non-visible light image stream, the first set being different than the second set.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary display mode table according to principles described herein.

DETAILED DESCRIPTION

Figure 1:
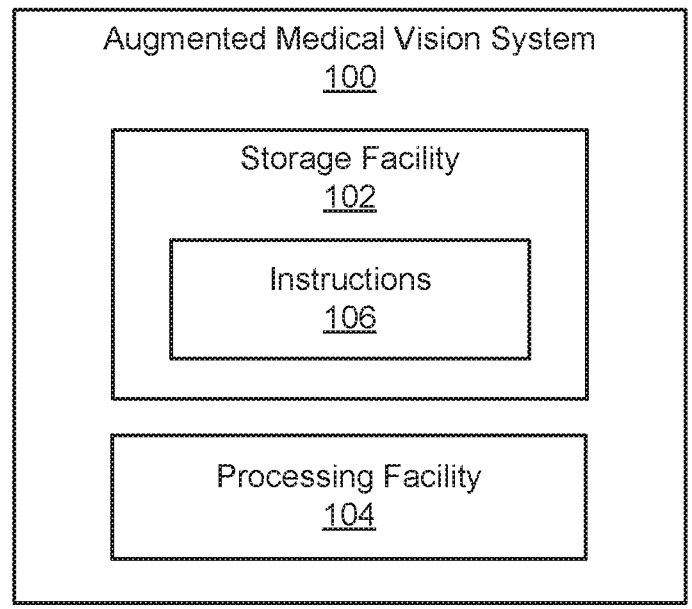
FIG. 1 illustrates an exemplary augmented medical vision system according to principles described herein.

Augmented medical vision systems and methods are described herein. As will be described below in more detail, an exemplary augmented medical vision system may direct an imaging device to continuously capture visible light (e.g., white light) and non-visible illumination (e.g., infrared fluorescence illumination and/or optical coherence tomography illumination) from a surgical area. The augmented medical vision system may generate a visible light image stream based on the captured visible light and an auxiliary image stream (e.g., a fluorescence image stream) based on the captured non-visible light. The augmented medical vision system may operate in a first display mode by generating and/or directing a display device to display a first video stream based on a first set of at least one of the visible light image stream and the auxiliary image stream. While operating in the first display mode, the augmented medical vision system may detect an event that occurs within the surgical area or work volume and switch, in response to the detection of the event, from operating in the first display mode to operating in a second display mode. When operating in the second display mode the augmented medical vision system may generate and/or direct the display device to display, in place of the first video stream, a second video stream based on a second set of at least one of the visible light image stream and the auxiliary image stream, the first set being different than the second set.

To illustrate, during a minimally-invasive surgical procedure involving a computer-assisted surgical system, an augmented medical vision system may present, while operating in a visible light display mode, an image of a surgical area captured under visible light by an endoscope. During the surgical procedure the surgeon may move a surgical instrument (e.g., a cautery instrument) to a position located within a predetermined distance of an anatomical feature (e.g., a major blood vessel) located within the surgical area. As a result, the augmented medical vision system may automatically switch from operating in the visible light display mode to operating in an augmented display mode or in a fluorescence display mode. In the augmented display mode or the fluorescence display mode, the anatomical feature may be highlighted with one or more contrasting colors (e.g., green) to enable the surgeon to easily detect the presence and location of the anatomical feature, thereby helping the surgeon to avoid unintended contact with or damage to the anatomical feature by the surgical instrument.

In the augmented display mode, an augmented image may take one of several different forms. In some examples, the augmented image may be a full-screen normal image (e.g., an image generated based on captured visible light) in which the anatomical feature is highlighted, based on captured non-visible illumination, with one or more contrasting colors.

Alternatively, the augmented image may include a picture-in-picture window displayed on a full-screen normal image. In some examples, the picture-in-picture window may display the normal image augmented with the highlighted anatomical feature. In alternative examples, the picture-in-picture window may overlay a portion of a full-screen normal color image and display a black-and-white image augmented with the highlighted anatomical feature. In some examples the augmented medical vision system may enable switching of the content of the full-screen window with the content of the picture-in-picture window. For example, a full-screen window may display a normal visible light image of the surgical scene and a picture-in-picture window may display an augmented image of the surgical scene. A user selection of a user interface element (e.g., on a user interface of a display device associated with a surgeon) may cause the full-screen window to display the augmented image of the surgical scene and the picture-in-picture window to display the normal visible light image. Another user selection of the user interface element may then return the images to their original window. In this way the user may easily maintain context of the surgical procedure but gain the benefit of seeing the highlighted anatomical feature when desired.

In other examples of the augmented image, a full-screen and/or picture-in-picture window may include text and/or graphical content (e.g., icons, shapes, patterns, arrows, etc.) identifying one or more anatomical features within view and/or providing information about the anatomical features.

As mentioned, the augmented medical vision system may direct the imaging device to continuously capture non-visible illumination from the surgical area and generate an auxiliary image stream based on the captured non-visible illumination. In some examples, the non-visible illumination may be fluorescence illumination having any wavelength outside the visible light spectrum. For example, the fluorescence illumination may have a wavelength in an infrared radiation region, such as a near-infrared ("NIR") radiation region, a short-wavelength infrared ("SWIR") radiation region, and a long-wavelength infrared ("LWIR") radiation region. In some examples, the non-visible illumination may have a wavelength of approximately 1000 nm or greater (e.g., SWIR and LAIR). Additionally or alternatively, the non-visible illumination may have a wavelength of about 350 nm or less (e.g., ultraviolet radiation). In some examples, the non-visible illumination may be specifically configured for optical coherence tomography imaging.

While the exemplary systems and methods that follow describe augmenting visible light imagery with fluorescence imagery (e.g., imagery based on a fluorescence image stream generated based on captured fluorescence illumination), the systems and methods are not limited to this configuration. For example, visible light imagery may additionally or alternatively be augmented with any other pre-operatively or intra-operatively captured imagery from imaging technology such as computed tomography, magnetic resonance imaging, fluoroscopy, thermography, ultrasound, optical coherence tomography, thermal imaging, impedance imaging, laser imaging, or nanotube X-ray imaging.

Various benefits may be realized by the systems and methods described herein. For example, the systems and methods described herein may automatically switch a display mode based on a detected context of a surgical procedure, which may improve a surgeon's efficiency by eliminating distractions involved with manually switching display modes. In some examples, the exemplary systems and methods described herein may automatically highlight, in an image of the surgical area, anatomical structures located within the surgical area when such information would be relevant to a surgeon but may be hard or impossible to see in a normal image. Moreover, in some examples, the exemplary systems and methods described herein may prevent injury or damage to patient tissue by automatically setting the appropriate display mode and/or disabling certain operations (e.g., cautery operations) based on the detected context of the procedure. These and other benefits that may be realized by the systems and methods described herein will be evident from the disclosure that follows.

FIG. 1 illustrates an exemplary augmented medical vision system 100 ("system 100"). As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). In some examples, facilities 102 and 104 may be distributed between multiple devices and/or multiple locations as may serve a particular implementation.

Storage facility 102 may maintain (e.g., store) executable data used by processing facility 104 to perform any of the operations described herein. For example, storage facility 102 may store instructions 106 that may be executed by processing facility 104 to perform any of the operations described herein. Instructions 106 may be implemented by any suitable application, software, code, and/or other executable data instance.

Storage facility 102 may also maintain any data received, generated, managed, used, and/or transmitted by processing facility 104. For example, as will be described below in more detail, storage facility 102 may maintain surgical session data, event data, display mode data (e.g., a display mode table), user profile data, and the like.

Processing facility 104 may be configured to perform (e.g., execute instructions 106 stored in storage facility 102 to perform) various processing operations associated with switching a display mode of system 100 based on a detected event that occurs within a surgical area (e.g., a surgical area associated with a patient). For example, processing facility 104 may direct an imaging device (e.g., an imaging device of a computer-assisted surgical system) to continuously capture visible light and fluorescence illumination from a surgical area. Processing facility 104 may further generate a visible light image stream based on the captured visible light and a fluorescence image stream based on the captured fluorescence illumination. Processing facility 104 may further operate in a first display mode by generating and/or directing a display device to display a first video stream based on a first set of at least one of the visible light image stream and the fluorescence image stream. Processing facility 104 may further detect, based on data (e.g., surgical session data) generated during the surgical session (e.g., during a surgical procedure), an event that occurs within the surgical area or work volume and switch, based on the detected event, from operating in the first display mode to operating in a second display mode. Alternatively to processing facility 104 detecting the event, another computing device or system may detect the event and transmit information associated with the detected event to processing facility 104, which may switch to operating in the second display mode in response to receiving the information associated with the detected event. Processing facility 104 may operate in the second display mode by generating and/or directing the display device to display, in place of the first video stream, a second video stream based on a second set of at least one of the visible light image stream and the fluorescence image stream, the first set being different than the second set. These and other operations that may be performed by processing facility 104 are described herein. In some implementations, system 100 may operate as part of or in conjunction with a computer-assisted surgical system. As such, an exemplary computer-assisted surgical system will now be described. The described exemplary computer-assisted surgical system is illustrative and not limiting. System 100 may operate as part of or in conjunction with the computer-assisted surgical system described herein and/or with other suitable computer-assisted surgical systems.

Figure 2:
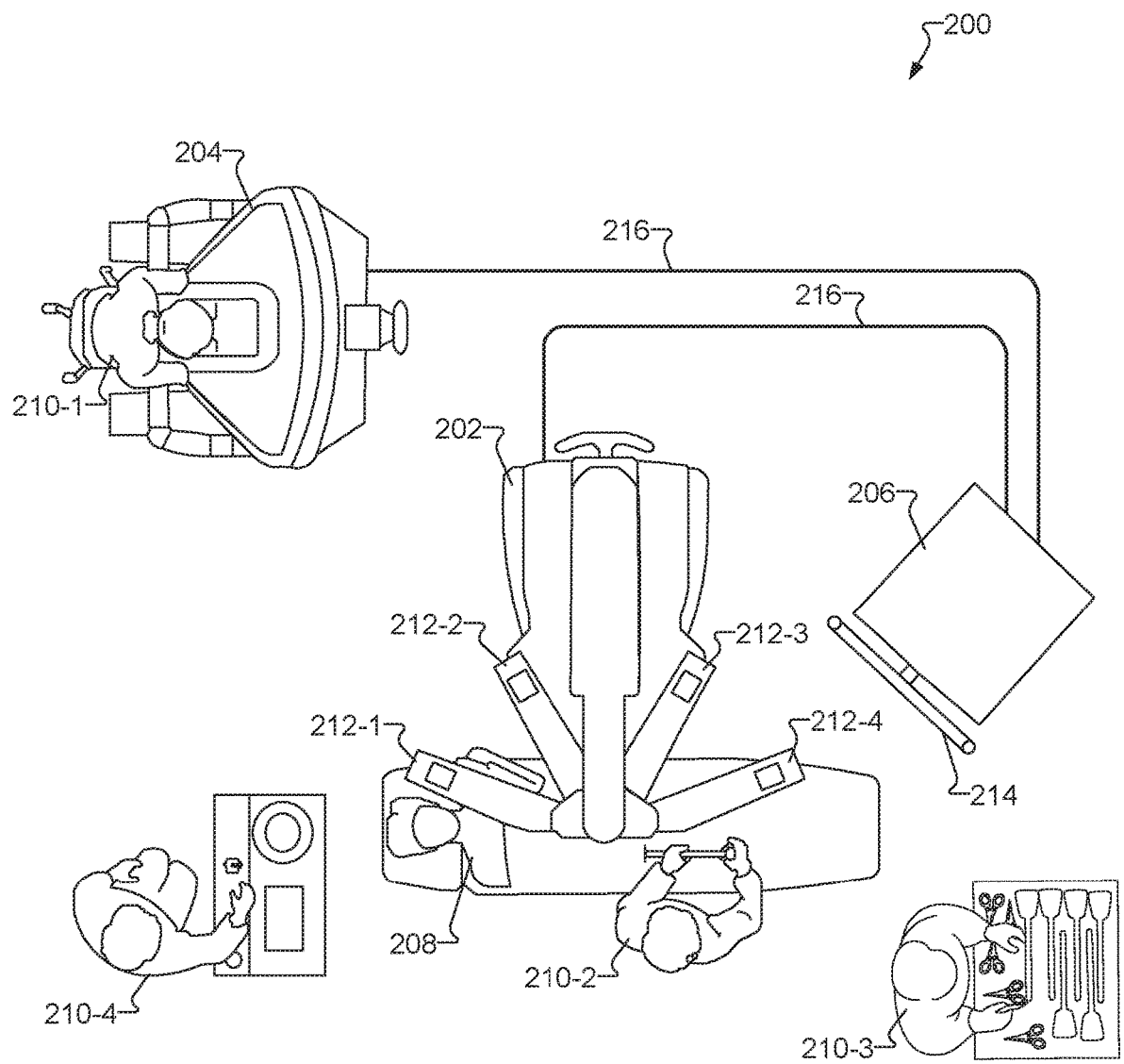
FIG. 2 illustrates an exemplary computer-assisted surgical system according to principles described herein.

FIG. 2 illustrates an exemplary computer-assisted surgical system 200 ("surgical system 200"), As shown, surgical system 200 may include a manipulating system 202, a user control system 204, and an auxiliary system 206 communicatively coupled one to another. In some examples, system 100 may be implemented by one or more of these components.

Surgical system 200 may be utilized by a surgical team to perform a computer-assisted surgical procedure on a patient 208. As shown, the surgical team may include a surgeon 210-1, an assistant 210-2, a nurse 210-3, and an anesthesiologist 210-4, all of whom may be collectively referred to as "surgical team members 210." Additional or alternative surgical team members may be present during a surgical session as may serve a particular implementation.

While FIG. 2 illustrates an ongoing minimally invasive surgical procedure, surgical system 200 may similarly be used to perform open surgical procedures or other types of surgical procedures that may similarly benefit from the accuracy and convenience of surgical system 200. Additionally, it will be understood that the surgical session throughout which surgical system 200 may be employed may not only include an operative phase of a surgical procedure, as is illustrated in FIG. 2, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any procedure that is not performed on a live patient, such as a calibration procedure, a training procedure, and an experimental or research procedure.

As shown in FIG. 2, manipulating system 202 may include a plurality of manipulator arms 212 (e.g., manipulator arms 212-1 through 212-4) to which a plurality of surgical instruments (not shown) may be coupled. Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure (e.g., by being at least partially inserted into patient 208 and manipulated to perform a computer-assisted surgical procedure on patient 208). While manipulating system 202 is depicted and described herein as including four manipulator arms 212, it will be recognized that manipulating system 202 may include only a single manipulator arm 212 or any other number of manipulator arms as may serve a particular implementation.

Manipulator arms 212 and/or surgical instruments attached to manipulator arms 212 may include one or more displacement transducers, orientational sensors, and/or positional sensors used to generate raw (i.e., uncorrected) kinematics information (hereinafter "surgical system sensors"). One or more components of surgical system 200 may be configured to use the kinematics information to track (e.g., determine positions of) and/or control the surgical instruments.

Surgical instruments attached to manipulator arms 212 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 200 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 204 may be configured to facilitate control by surgeon 210-1 of manipulator arms 212 and surgical instruments attached to manipulator arms 212. For example, surgeon 210-1 may interact with user control system 204 to remotely move or manipulate manipulator arms 212 and the surgical instruments. To this end, user control system 204 may provide surgeon 210-1 with imagery (e.g., high-definition 3D imagery) of a surgical area associated with patient 208 as captured by an endoscope. In certain examples, user control system 204 may include a stereo viewer having two displays where stereoscopic images of a surgical area associated with patient 208 and generated by a stereoscopic imaging system may be viewed by surgeon 210-1. Surgeon 210-1 may utilize the imagery to perform one or more procedures with one or more surgical instruments attached to manipulator arms 112.

To facilitate control of surgical instruments, user control system 204 may include a set of master controls (not shown). These master controls may be manipulated by surgeon 210-1 to control movement of surgical instruments (e.g., by utilizing robotic and/or teleoperation technology). The master controls may be configured to detect a wide variety of hand, wrist, and finger movements by surgeon 210-1. In this manner, surgeon 210-1 may intuitively perform a surgical procedure using one or more surgical instruments.

User control system 204 may further be configured to facilitate control by surgeon 210-1 of other components of surgical system 200. For example, surgeon 210-1 may interact with user control system 204 to change a configuration or operating mode of surgical system 200, to change a display mode of surgical system 200, to generate additional control signals used to control surgical instruments attached to manipulator arms 212, to facilitate switching control from one surgical instrument to another, or to perform any other suitable operation. To this end, user control system 204 may also include one or more input devices (e.g., foot pedals, buttons, switches, etc.) configured to receive input from surgeon 210-1.

Auxiliary system 206 may include one or more computing devices configured to perform primary processing operations of surgical system 200. The one or more computing devices included in auxiliary system 206 may control and/or coordinate operations performed by various other components (e.g., manipulating system 202 and/or user control system 204) of surgical system 200. For example, a computing device included in user control system 204 may transmit instructions to manipulating system 202 by way of the one or more computing devices included in auxiliary system 206. As another example, auxiliary system 206 may receive, from manipulating system 202 (e.g., from an imaging device), and process image data representative of imagery captured by an endoscope attached to one of manipulator arms 212.

In some examples, auxiliary system 206 may be configured to present visual content to surgical team members 210 who may not have access to the images provided to surgeon 210-1 at user control system 204. To this end, auxiliary system 206 may include a display monitor 214 configured to display one or more user interfaces, such as images (e.g., 2D images) of the surgical area, information associated with patient 208 and/or the surgical procedure, and/or any other visual content as may serve a particular implementation. For example, display monitor 214 may display images of the surgical area together with additional content (e.g., graphical content, contextual information, etc.) concurrently displayed with the images. In some embodiments, display monitor 214 is implemented by a touchscreen display with which surgical team members 210 may interact (e.g., by way of touch gestures) to provide user input to surgical system 200.

Manipulating system 202, user control system 204, and auxiliary system 206 may be communicatively coupled one to another in any suitable manner, For example, as shown in FIG. 2, manipulating system 202, user control system 204, and auxiliary system 206 may be communicatively coupled by way of control lines 216, which may represent any wired or wireless communication link as may serve a particular implementation. To this end, manipulating system 202, user control system 204, and auxiliary system 206 may each include one or more wired or wireless communication interfaces, such as one or more local area network interfaces, Wi-Fi network interfaces, cellular interfaces, etc.

Figure 3:
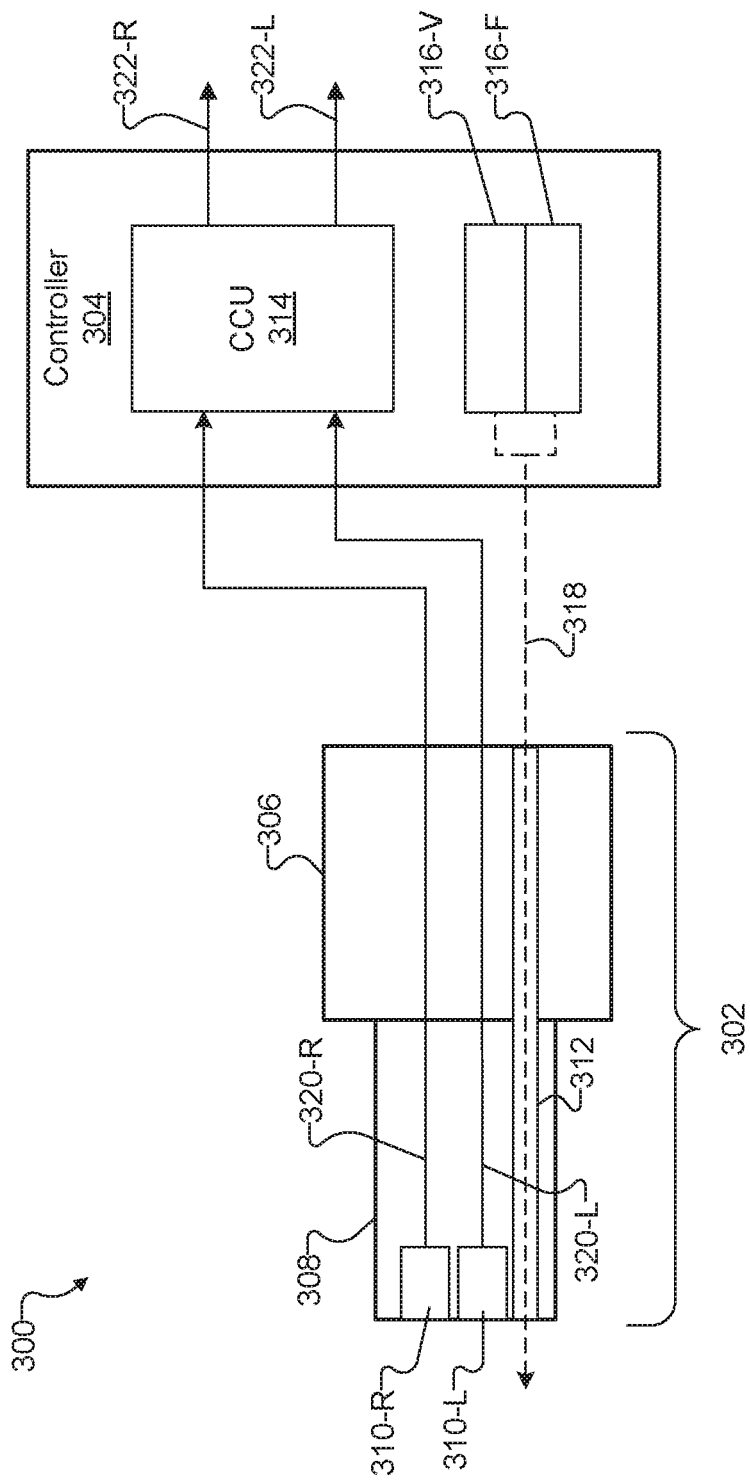
FIG. 3 illustrates an exemplary imaging system that may be used with the computer-assisted surgical system of FIG. 2 according to principles described herein.

FIG. 3 illustrates a functional diagram of an exemplary imaging system 300 that may be used in accordance with the systems and methods described herein to capture images of a scene (e.g., a surgical area associated with patient 208). As shown, imaging system 300 includes an imaging device 302 and a controller 304. Imaging system 300 may include additional or alternative components as may serve a particular implementation. For example, imaging system 300 may include various optical and/or electrical signal transmission components (e.g., wires, lenses, optical fibers, choke circuits, waveguides, etc.), a cable that houses electrical wires and/or optical fibers and that is configured to interconnect imaging device 302 and controller 304, etc.

Imaging device 302 may be implemented by an endoscope or other camera device configured to capture images of a scene. As shown, imaging device 302 includes a camera head 306, a shaft 308 coupled to and extending away from camera head 306, image sensors 310 (e.g., a right-side image sensor 310-R and a left-side image sensor 310-L) at a distal end of shaft 308, and an illumination channel 312. In the example of FIG. 3, imaging device 302 is stereoscopic. Alternatively, in other examples imaging device 302 may be monoscopic (e.g., by including one image sensor 310 instead of two image sensors 310).

Imaging device 302 may be manually handled and controlled (e.g., by a surgeon performing a surgical procedure on a patient). Alternatively, camera head 306 may be coupled to a manipulator arm (e.g., one of manipulator arms 112) of a computer-assisted surgical system (e.g., surgical system 100) imaging device 302 and controlled using robotic and/or teleoperation technology.

The distal end of shaft 308 may be positioned at or near a scene that is to be imaged by imaging device 302. For example, the distal end of shaft 308 may be inserted into a patient. In this configuration, imaging device 302 may be used to capture images of anatomy and/or other objects within the scene.

Image sensors 310 may each be implemented by any suitable image sensor, such as a charge coupled device ("CCD") image sensor, a complementary metal-oxide semiconductor ("CMOS") image sensor, or the like. In some examples, as shown in FIG. 3, image sensors 310 are positioned at the distal end of shaft 308. Alternatively, image sensors 310 may be positioned closer to a proximal end of shaft 308, inside camera head 306, or outside imaging device 302 (e.g., inside controller 304). In these alternative configurations, optics (e.g., lenses, optical fibers, etc.) included in shaft 308 and/or camera head 306 may convey light from a scene to image sensors 310.

Image sensors 310 are configured to detect (e.g., capture, collect, sense, or otherwise acquire) light. For example, image sensor 310-R is configured to detect the light from a right-side perspective, and image sensor 310-L is configured to detect the light from a left-side perspective. The light detected by image sensors 310 may include, for example, visible light reflected by an object included within the scene and/or fluorescence illumination emitted by a fluorescence imaging agent (e.g., a fluorescent dye, a fluorophore, or a fluorescent protein that has been injected or absorbed into a bloodstream of a patient) within the scene. In some examples, the fluorescence illumination has a wavelength in an infrared light region (e.g., in an NIR region). As will be illustrated below, image sensors 310 may convert the detected light into data representative of one or more images.

In some examples, imaging device 302 may include, in addition to image sensors 310, an auxiliary sensor (not shown) configured to detect light to be used in augmenting imagery generated based on light captured by image sensors 310. The auxiliary sensor may be implemented by one or more image sensors, which may each be a CCD image sensor, a CMOS image sensor, or the like. In some examples, the auxiliary sensor may include a pair of image sensors configured to capture stereoscopic imagery. The auxiliary sensor may be positioned at the distal end of shaft 308, or it may alternatively be positioned closer to the proximal end of shaft 308, inside camera head 306, or outside imaging device 302 (e.g., inside controller 304). In these alternative configurations, optics included in shaft 308 and/or camera head 306 may convey light from the scene to the auxiliary sensor. In some examples, the auxiliary sensor may share optics with image sensors 310.

The auxiliary sensor may capture imagery of all or part of the scene captured by image sensors 310. In some examples the field of view of the auxiliary sensor may be the same as image sensors 310 but may differ slightly (due to its position within shaft 308) without loss of utility. In some examples the auxiliary sensor may detect non-visible light (e.g., ultraviolet light and/or infrared radiation in the SWIR or LWIR bands). Additionally or alternatively, the auxiliary sensor may capture imagery in other imaging domains, such as optical coherence tomography.

Illumination channel 312 may be implemented by one or more optical components (e.g., optical fibers, light guides, lenses, etc.). As will be described below, illumination may be provided to the scene by way of illumination channel 312 to illuminate a scene.

Controller 304 may be implemented by any suitable combination of hardware and software configured to control and/or interface with imaging device 302. For example, controller 304 may be at least partially implemented by a computing device included in auxiliary system 106. Controller 304 may also include optical and/or electrical interfaces for communicating with any auxiliary sensor.

Controller 304 includes a camera control unit ("CCU") 314 and illumination sources 316 (e.g., a visible light illumination source 316-V and a fluorescence excitation illumination source 316-F). Controller 304 may include additional or alternative components as may serve a particular implementation. For example, controller 304 may include circuitry configured to provide power to components included in imaging device 302. In some examples, CCU 314 and/or illumination source 316 are alternatively included in imaging device 302 (e.g., in camera head 306).

CCU 314 is configured to control various parameters (e.g., activation times, auto exposure, etc.) of image sensors 310. As will be described below, CCU 314 may be further configured to receive and process image data from image sensors 310, While CCU 314 is shown in FIG. 3 to be a single unit, CCU 314 may alternatively be implemented by a first CCU configured to control right-side image sensor 310-R and a second CCU configured to control left-side image sensor 310-L.

Illumination sources 316 may be configured to generate and emit illumination 318. Illumination 318 (which is also referred herein to as light) may travel by way of illumination channel 312 to a distal end of shaft 308, where illumination 318 exits to illuminate a scene.

Illumination generated by illumination source 316-V may include visible light having one or more color components or a continuous spectrum of light (e.g., white light). Illumination generated by illumination source 316-F may include fluorescence excitation illumination configured to excite a fluorescence imaging agent to emit fluorescence illumination. In some examples, the fluorescence excitation illumination has a wavelength in an infrared light region (e.g., in a near-infrared light region). While each illumination source 316 is shown to be a single device in controller 304, each illumination source 316 may alternatively include multiple illumination sources each configured to generate and emit differently configured illumination. In some examples, illumination source 316-V may also generate illumination tailored to the requirements of any auxiliary sensor included in imaging device 302 to provide suitable illumination or patterns for the auxiliary sensor.

To capture one or more images of a scene, controller 304 (or any other suitable computing device) may activate illumination sources 316 and image sensors 310. While activated, illumination sources 316 concurrently emit illumination 318, which travels via illumination channel 312 to the scene. Image sensors 310 detect visible light illumination reflected from one or more surfaces in the scene and detect fluorescence illumination that is emitted by the fluorescence imaging agent excited by the fluorescence excitation illumination.

Image sensors 310 (and/or other circuitry included in imaging device 302) may convert the detected light into image data 320 representative of one or more images of the scene. For example, image sensor 310-R outputs image data 320-R representative of images captured from a right-side perspective and image sensor 310-L outputs image data 320-L representative of images captured from a left-side perspective. Image data 320 may have any suitable format. Similarly, any auxiliary sensor may convert the detected light into auxiliary image data representative of one or more auxiliary images of the scene (e.g., fluorescence images, optical coherence tomography images, etc.).

Image data 320 is transmitted from image sensors 310 to CCU 314. Image data 320 may be transmitted by way of any suitable communication link between image sensors 310 and CCU 314. For example, image data 320 may be transmitted by way of wires included in a cable that interconnects imaging device 302 and controller 304. Additionally or alternatively, image data 320 may be transmitted by way of one or more optical fibers. Data from any auxiliary sensor may similarly be transmitted to CCU 314 by way of a suitable communication link.

CCU 314 may process (e.g., packetize and/or format) image data 320 (and, optionally, auxiliary image data) and output processed image data 322 (e.g., processed image data 322-R corresponding to image data 320-R and processed image data 322-L corresponding to image data 320-L). Processed image data 322 may be transmitted to an image processor (not shown) for further processing. The image processor may be implemented by one or more computing devices external to imaging system 300, such as one or more computing devices included in surgical system 200 (e.g., in one or more computing devices included within auxiliary system 206). In some examples, the image processor is implemented by processing facility 104 of system 100. Alternatively, the image processor may be included in controller 304. The image processor may prepare processed image data 322 for display on one or more display devices (e.g., in the form of one or more still images and/or video content). For example, the image processor may generate, based on the visible light detected by image sensors 310, a plurality of visible light images, which may be sequentially output to form a visible light image stream. The visible light images may include full color images and/or grayscale images. The image processor may also generate, based on the fluorescence illumination detected by image sensors 310, a plurality of fluorescence images, which may be sequentially output to form a fluorescence image stream. In some examples, the fluorescing regions in the fluorescence images may be artificially colored (pseudo-colored), such as green or blue, to highlight the fluorescing regions when the fluorescence image stream is displayed by the display device. Additionally, the image processor may be configured to selectively apply a gain to a fluorescence image to adjust (e.g., increase or decrease) the illumination intensity of the fluorescing regions of the fluorescence image stream.

After and/or during generation of the visible light image stream and the fluorescence image stream by the image processor, system 100 may direct a display device (e.g., a stereo viewer of user control system 204 and/or display monitor 214 of auxiliary system 206) to display a video stream based on a set of at least one of the visible light stream and the fluorescence image stream. System 100 may operate in one of a plurality of display modes each based on a unique set of the visible light stream and/or the fluorescence image stream.

Figure 4:
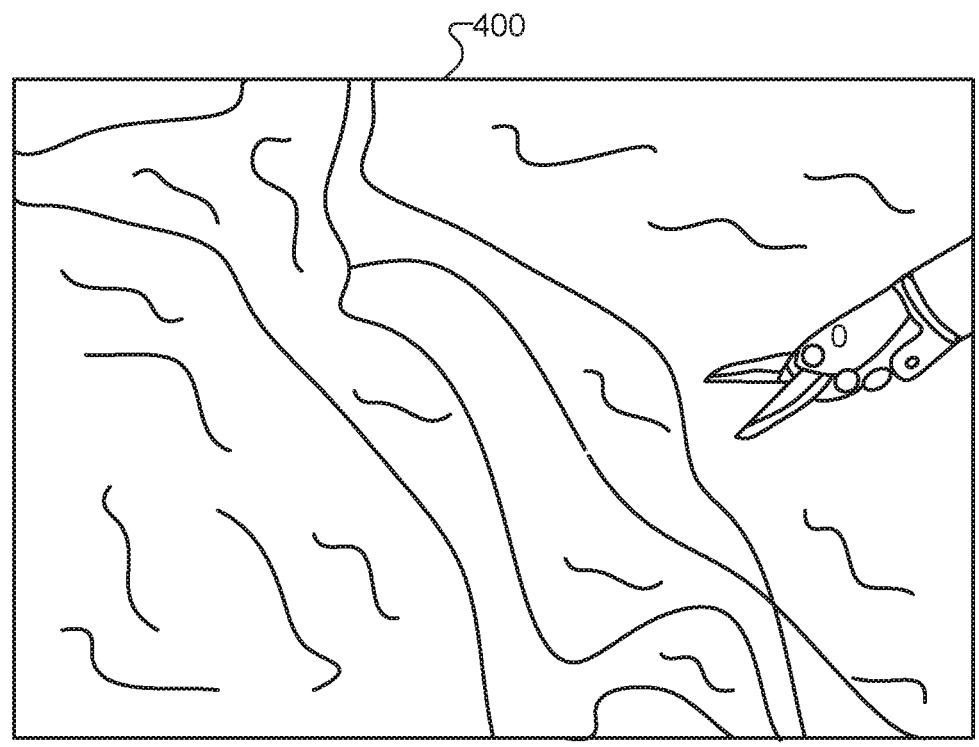
FIG. 4 illustrates an exemplary image of a surgical area during a visible light display mode according to principles described herein.

For example, when system 100 operates in a visible light display mode, system 100 directs the display device to display a video stream based only on the visible light image stream generated by the image processor. FIG. 4 illustrates an exemplary image 400 displayed by the display device when system 100 is operating in the visible light display mode. As shown, image 400 depicts the surgical area as captured by the imaging device under visible light. Image 400 may be a full-color image or a grayscale image as may serve a particular implementation.

Figure 5:
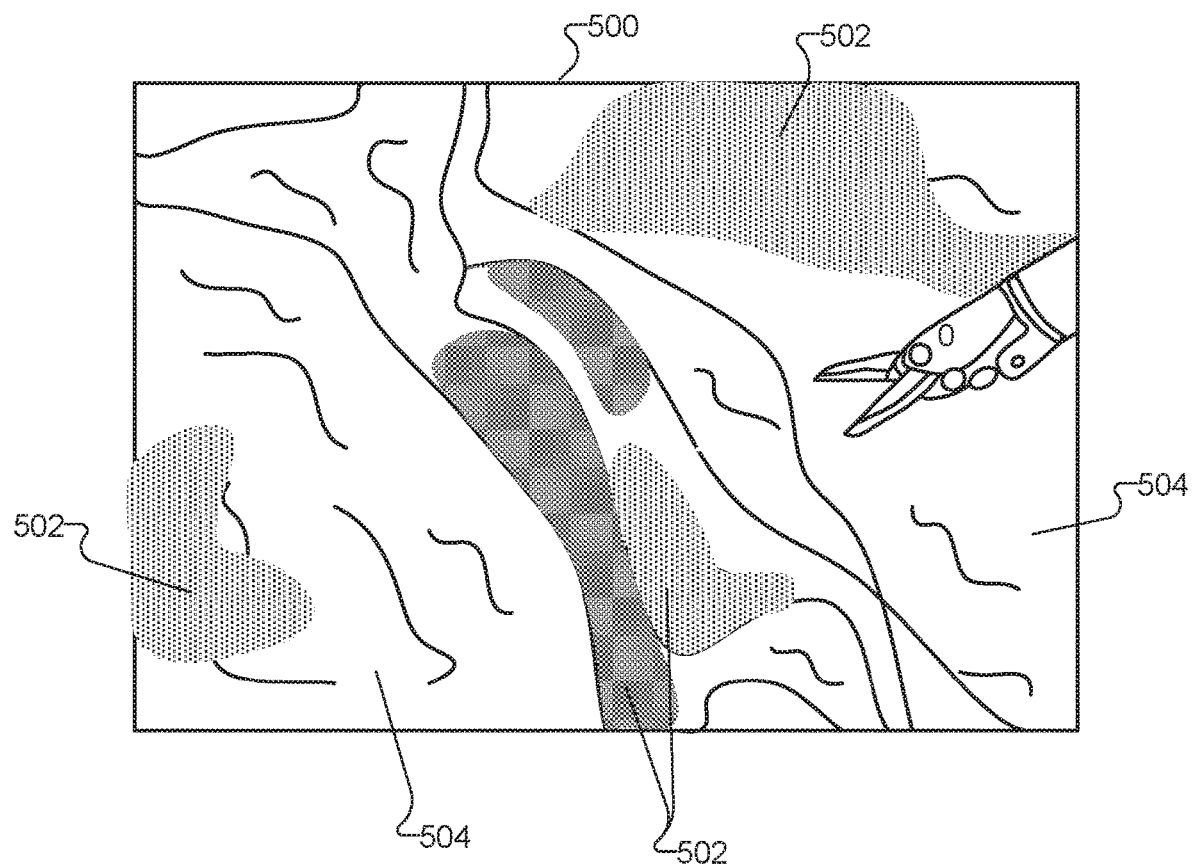
FIG. 5 illustrates an exemplary image of a surgical area during an augmented display mode according to principles described herein.

When system 100 operates in an augmented display mode, the visible light image stream is augmented with the fluorescence image stream. To this end, system 100 directs the display device to display a video stream based on a combination of the visible light image stream and the fluorescence image stream. The visible light image stream and the fluorescence image stream may be combined in any suitable manner, such as by superimposing fluorescence images on visible light images, blending (e.g., alpha blending), and the like. FIG. 5 illustrates an exemplary image 500 displayed by the display device when system 100 is operating in the augmented display mode. Image 500 depicts the same scene as image 400. However, image 500 includes fluorescent regions 502 (the shaded regions in FIG. 5) superimposed on visible light regions 504. As shown, image 500 depicts the surgical area as captured by the imaging device under both visible light and fluorescence illumination. As explained above, fluorescent regions 502 may be displayed in an artificial color (e.g., green or blue). In this way certain anatomical features located within the surgical area may be highlighted, such as organs or blood vessels.

Figure 6:
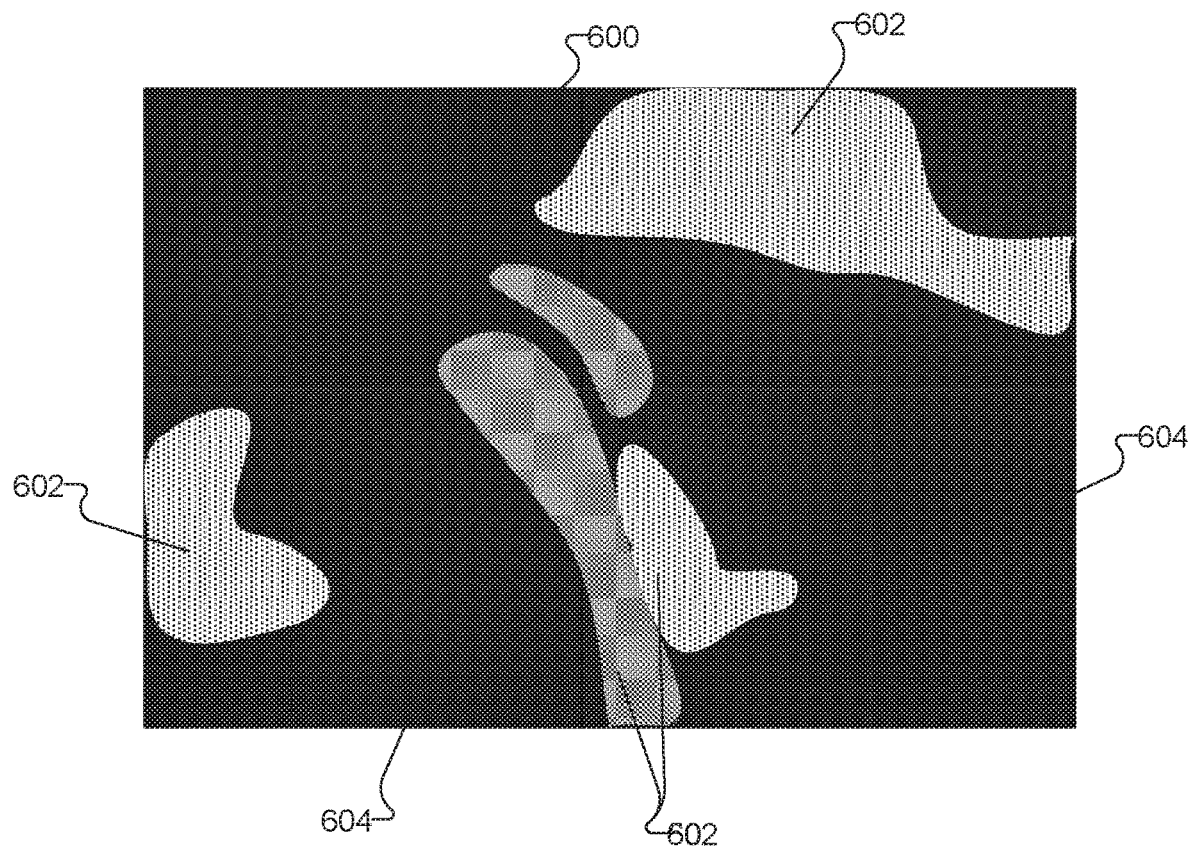
FIG. 6 illustrates an exemplary image of a surgical area during a fluorescence display mode according to principles described herein.

When system 100 operates in a fluorescence display mode, system 100 directs the display device to display a video stream based only on the fluorescence image stream. FIG. 6 illustrates an exemplary image 600 displayed by the display device when system 100 is operating in the fluorescence display mode. Image 600 depicts the same scene as images 400 and 500. However, image 600 shows only fluorescent regions 602 on dark regions 604 (i.e., regions of image 600 that do not fluoresce) because image 600 depicts the surgical area as captured by the imaging device under only fluorescence excitation illumination. In fluorescence mode, fluorescent regions 602 in image 600 have greater contrast than fluorescent regions 502 in image 500, thus further highlighting the anatomical features located within the surgical area.

An image of any display mode be rendered as a full-screen image or, alternatively, as a picture-in-picture window superimposed on an image of a different display mode. For example, an augmented image (e.g., image 500) may be rendered as a picture-in-picture window superimposed on a normal image (e.g., image 400), or vice versa.

In some examples, imagery (e.g., fluorescence imagery or optical coherence tomography imagery) used to augment the visible light image may be captured from an auxiliary sensor included in the imaging device (e.g., an auxiliary sensor included in imaging device 302).

While system 100 has been shown in FIGS. 4-7 to operate in three display modes, system 100 may alternatively operate in fewer or more display modes. For example, system 100 may generate multiple different visible light image streams based on different color components. Additionally or alternatively, system 100 may generate multiple different fluorescence image streams based on different fluorescence illumination wavelengths emitted from the surgical area.

Figure 7:
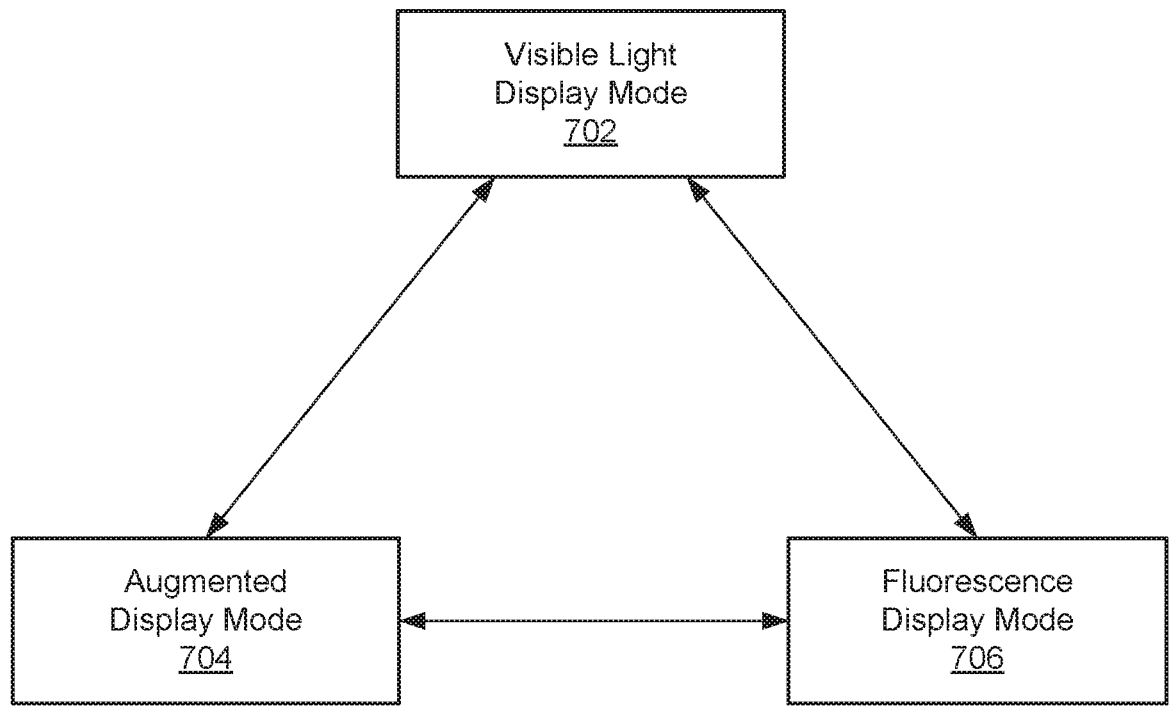
FIG. 7 illustrates an exemplary manner in which display modes may be switched according to principles described herein.

System 100 may automatically switch between different display modes based on a detected context of a scene captured by the imaging device. FIG. 7 illustrates an exemplary manner in which system 100 may switch a display mode. When system 100 (or any other suitable computing system) detects an event that occurs within a surgical area while system 100 is operating in a visible light display mode 702, system 100 may switch to an augmented display mode 704 or to a fluorescence display mode 706. When system 100 (or any other suitable computing system) detects an event that occurs within the surgical area while system 100 is operating in augmented display mode 704, system may switch to visible light display mode 702 or to fluorescence display mode 706. When system 100 (or any other suitable computing system) detects an event that occurs within the surgical area while system 100 is operating in fluorescence display mode 706, system 100 may switch to visible light display mode 702 or to augmented display mode 704.

As will be described below in more detail, the display mode to which system 100 will switch may be determined based on various parameters, including but not limited to the type of event detected, the type of a surgical instrument causing the event, the current display mode, a user profile of a user (e.g., a surgeon) logged in to system 100, and the like.

Various operations that may be performed by system 100 (e.g., by processing facility 104 of system 100) to automatically switch between different display modes, and examples of these operations, will now be described. It will be recognized that the operations and examples described herein are merely illustrative of the many different types of operations that may be performed by system 100.

System 100 (e.g., processing facility 104 of system 100) may direct an imaging device (e.g., imaging device 302 of imaging system 300) to continuously capture visible light from a scene (e.g., a surgical area associated with a patient) and fluorescence illumination from the scene. In some examples, system 100 may direct the imaging device to continuously capture the visible light and the fluorescence illumination simultaneously. When the visible light and the fluorescence illumination are captured simultaneously, they represent the same state of the scene, System 100 may further generate a visible light image stream based on the captured visible light and generate a fluorescence image stream based on the captured fluorescence illumination. System 100 may generate the visible light image stream and the fluorescence image stream in any suitable way. For example, an image processor may access processed image data (e.g., processed image data 322) from an imaging system (e.g., imaging system 300) and separate a visible light component of the processed image data from a fluorescence illumination component of the processed image data. System 100 may generate the visible light image stream based on the visible light component of the processed image data, and may generate the fluorescence image stream based on the fluorescence illumination component of the processed image data.

While system 100 is operating in the first display mode, system 100 may access surgical session data generated during a surgical session and, based on the surgical session data, detect an event that occurs within a surgical area.

In some examples, surgical session data accessed by system 100 may be generated during the surgical session and may be based on one or more operations performed by a computer-assisted surgical system (e.g., surgical system 200) during the surgical session. The operations performed by the computer-assisted surgical system may include any mechanical, electrical, hardware, and/or software-based operations as may serve a particular implementation. The surgical session data may be generated by the computer-assisted surgical system (e.g., by one or more components within surgical system 200), by one or more components coupled to the computer-assisted surgical system during the surgical session (e.g., one or more surgical instruments attached to one or more manipulator arms 212), by one or more user devices communicatively paired with the computer-assisted surgical system during the surgical session, and/or by any other device associated with the computer-assisted surgical system as may serve a particular implementation.

The surgical session data may include any data generated during a surgical session associated with a patient. For example, the surgical session data may include kinematic data, image data, depth data, sensor data, surgical instrument data, and/or any other type of data as may serve a particular implementation.

Kinematic data may be representative of a position, a pose, and/or an orientation of a component within the computer-assisted surgical system and/or a component coupled to the computer-assisted surgical system. For example, kinematic data may be representative of a position, a pose, and/or an orientation of a manipulator arm 212 and/or a surgical instrument attached to manipulator arm 212.

Image data may be representative of one or more images captured by an imaging device coupled to the computer-assisted surgical system. For example, image data may be representative of one or more images captured by imaging device 302 (e.g., by imaging sensors 310 and/or one or more auxiliary sensor(s)) coupled to a manipulator arm 212. The one or more images may constitute one or more still images and/or video streams captured by the imaging device. In some examples, system 100 may access processed image data 322 output by CCU 314 of imaging system 300. Additionally or alternatively, system 100 may access visible light images and/or fluorescence images output by an image processor coupled to CCU 314.

Depth data may be representative of depth of a surgical area, or may be data that may be processed to derive depth data of the surgical area. For example, imaging device 302 may capture images of the surgical area that represent depth sensed by imaging device 302. Alternatively, images captured by imaging device 302 may be processed to derive depth data of the surgical area. For example, processed images 322-R and 322-L may be stereoscopic images of the surgical area and may be processed (e.g., by an image processor) to determine depth information for the surgical area. The depth information may be represented as depth images (e.g., depth map images obtained using a Z-buffer that indicates distance from imaging device 302 to each pixel point on an image of a surgical area), which may be configured to visually indicate depths of objects in the surgical area in any suitable way, such as by using different greyscale values to represent different depth values.

Sensor data may include any data generated by sensors (e.g., surgical system sensors) included in or associated with a computer-assisted surgical system. Sensor data may be representative of any sensed parameter as may serve a particular implementation. For example, sensor data may be indicative of whether a surgical instrument attached to a manipulator arm 212 is idle or is currently moving.

Surgical instrument data may include any data generated by a surgical instrument (e.g., a surgical instrument attached to a manipulator arm 214) and may be representative of an identifier of the surgical instrument, an operational state of the surgical instrument (e.g., open, closed, electrically charged, idle, etc.), a fault code of the surgical instrument, etc.

System 100 may detect an event that occurs within a surgical area based on surgical session data generated during the surgical session. An event that occurs within a surgical area may include any distinct operation or action that occurs within the surgical area during the surgical session. Exemplary events that occur within a surgical area may include an operation of a surgical instrument located within the surgical area (a "surgical instrument operation"), an idle state event, and/or a fluorescence event.

Surgical instrument operations may include, but are not limited to, operation of a tissue interaction functionality of the surgical instrument, operation of a sensing functionality of the surgical instrument, and movement of a surgical instrument.

A tissue interaction functionality of a surgical instrument may include any functionality that enables the surgical instrument to interact with patient tissue, such as grasping tissue, cutting tissue, repairing tissue, suturing tissue, stapling tissue, clipping tissue, sealing tissue, cauterizing tissue, and the like. Accordingly, exemplary surgical instrument operations may include, without limitation, opening or closing a forceps instrument, a grasper instrument, a retractor instrument, a scissors or shears instrument, a clip applier instrument, a dissector instrument, and/or a needle driver instrument; energizing a cautery instrument or an ultrasonic instrument; firing a stapling instrument; and the like.

A sensing functionality of a surgical instrument may include any functionality that enables the surgical instrument (e.g., a probe) to sense a feature, state, or condition of an object (e.g., patient tissue). For example, a sensing functionality may include, without limitation, ultraviolet light, visible light, and infrared light sensing; ultrasound sensing; optical coherence tomography (OCT); computed tomography (CT); magnetic resonance imaging (MRI); and the like.

A movement of a surgical instrument may include any change in a position, a pose, and/or an orientation of the surgical instrument. Accordingly, a surgical instrument operation may include, without limitation, a translational movement of a surgical instrument from a first location within a surgical area to a second location within the surgical area, and a rotational movement of the surgical instrument within the surgical area.

In some examples, a surgical instrument operation may include movement of a surgical instrument to a particular position within the surgical area. In some examples, a surgical instrument operation may include movement of a surgical instrument to a position outside the field of view of an imaging device located at the surgical area. In additional examples, a surgical instrument operation may include movement of a surgical instrument to a position located within a predetermined distance of an anatomical feature (e.g., an organ, a blood vessel, a tumor, etc.) located at the surgical area. Exemplary methods and systems for determining movement of a surgical instrument to a particular position within the surgical area will be described in more detail below.

Idle state events may include the absence, for a predetermined period of time, of a surgical instrument operation, e.g., operation of a tissue interaction functionality of a surgical instrument, operation of a sensing functionality of the surgical instrument, and/or a movement of the surgical instrument. For example, an idle state event may include the passage of a predetermined period of time (e.g., 10 seconds) without translational and/or rotational movement of a surgical instrument located within the surgical area. As another example, an idle state event may include the passage of a predetermined period of time (e.g., 30 seconds) without energization of a cautery instrument.

Fluorescence events may include events that occur based on fluorescence excitation within the surgical area. In some examples, fluorescence events may include a change in an intensity of fluorescence illumination emitted from the surgical area. For instance, a fluorescence event may include a determination by system 100 that an intensity of fluorescence illumination emitted from the surgical area has reached (e.g., has increased or decreased) a predetermined threshold value. Additionally or alternatively, a fluorescence event may include a determination by system 100 that the intensity of the fluorescence illumination emitted from the surgical area has changed by more than a predetermined amount.

System 100 may determine the intensity of the fluorescence illumination in any suitable way. For example, system 100 may determine the intensity of the fluorescence illumination as the maximum illumination intensity of a pixel or a group of pixels in the fluorescence image stream. Alternatively, system 100 may determine the intensity of the fluorescence illumination as the average illumination intensity of a group of pixels in the fluorescence image stream.

Another example of a fluorescence event may include a change in a level of a fluorescence imaging agent within the surgical area. To illustrate, after a fluorescence imaging agent is administered to the patient (e.g., injected into the bloodstream), the concentration of the fluorescence imaging agent within the bloodstream at the surgical area gradually increases over time as the fluorescence imaging agent moves in the bloodstream to the surgical area. After a generally brief period of time (e.g., a few minutes) the concentration of the fluorescence imaging agent in the bloodstream at the surgical area may reach a steady state or a concentration sufficient for fluorescence illumination emitted by the fluorescence imaging agent to be detected by an imaging device. Thus, a fluorescence event may include the passage of a predetermined period of time (e.g., two minutes) after the fluorescence imaging agent is administered to the patient.

As mentioned above, system 100 may detect an event that occurs within a surgical area based on surgical session data and switch, in response to the detection of the event, the display mode. For example, system 100 may operate in a first display mode (e.g., a visible light display mode, an augmented display mode, or a fluorescence display mode) by directing a display device to display a first video stream based on a first set of at least one of a visible light image stream and a fluorescence image stream. System 100 may further detect, while operating in the first display mode, an event that occurs within a surgical area. In response to detecting the event, system 100 may direct the display device to display a second video stream based on a second set of at least one of the visible light image stream and the fluorescence image stream, the first set being different than the second set. These operations may be performed in any suitable manner.

Figure 8:
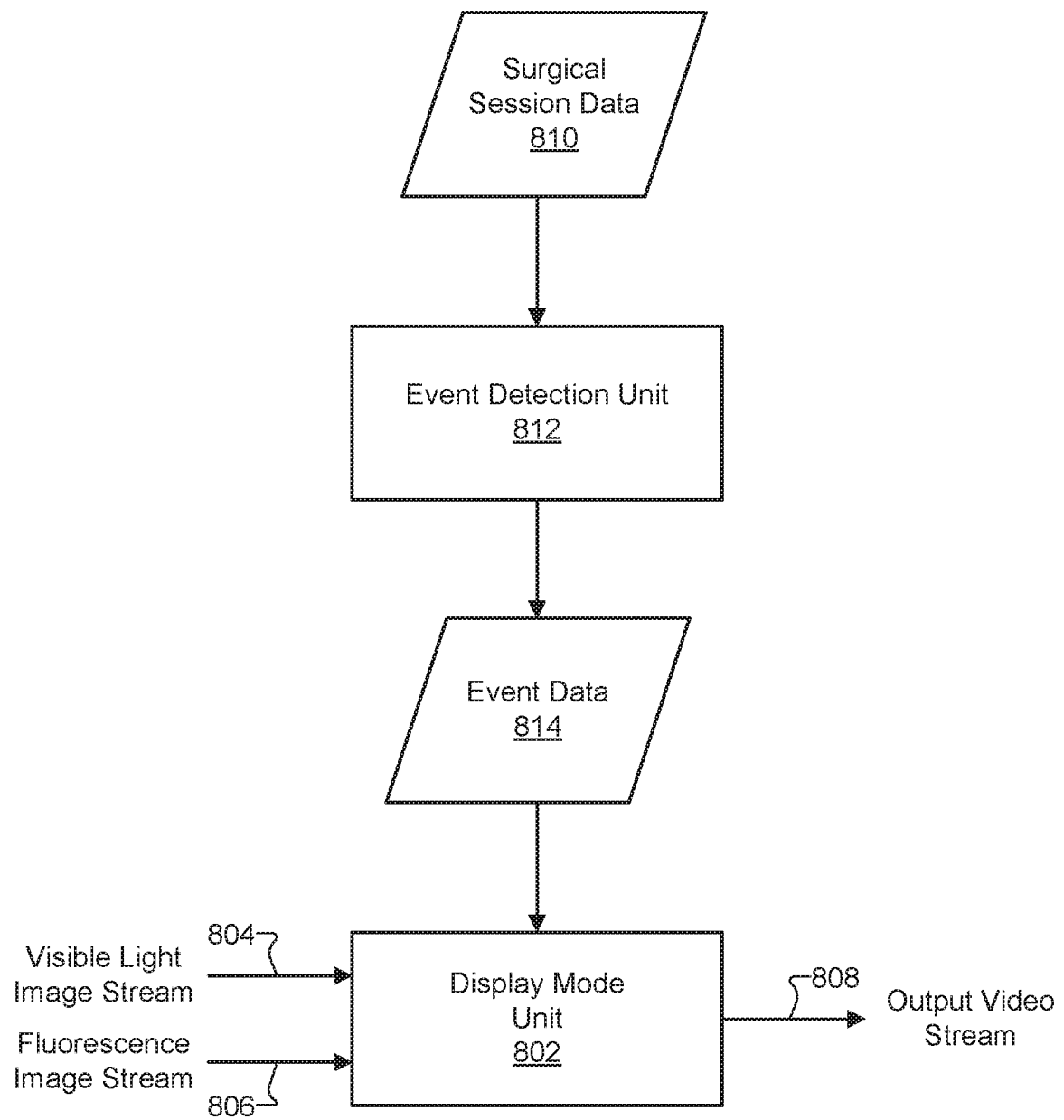
FIG. 8 illustrates an exemplary manner in which an event may be detected and a display mode may be switched in response to the detection of the event according to principles described herein.

FIG. 8 illustrates an exemplary manner in which system 100 may detect, while operating in a first display mode, an event based on surgical session data and switch, in response to the detection of the event, from operating in the first display mode to operating in the second display mode.

As shown, a display mode unit 802 receives (e.g., from an image processor communicatively coupled with imaging system 300) a visible light image stream 804 and a fluorescence image stream 806 and generates, based on visible light image stream 804 and/or fluorescence image stream 806, an output video stream 808 for display by a display device (e.g., stereo viewer of user control system 204 and/or display monitor 214 of auxiliary system 206). While system 100 is operating in a first display mode, output video stream 808 is a first video stream based on a first set of at least one of visible light image stream 804 and fluorescence image stream 806. For example, when the first display mode is visible light display mode 702, the first video stream is based only on visible light image stream 804. When the first display mode is augmented display mode 704, the first video stream is an augmented stream based on a combination of visible light image stream 804 and fluorescence image stream 806. When the first display mode is fluorescence display mode 706, the first video stream is based only on fluorescence image stream 808.

While system 100 is operating in the first display mode, system 100 may apply surgical session data 810 as an input to an event detection unit 812. Event detection unit 812 may analyze surgical session data 810 and detect an event that occurs within the surgical area. Event detection unit 812 may perform any suitable heuristic, process, and/or operation that may be performed or executed by system 100 and that may be configured detect an event based on surgical session data 810. In some examples, event detection unit 812 may be implemented by hardware and/or software components (e.g., processors, memories, communication interfaces, instructions stored in memory for execution by the processors, etc.), such as storage facility 102 and/or processing facility 104 of system 100.

Event detection unit 812 may detect an indicator and/or a pattern in surgical session data 810 that is indicative of an occurrence of a particular event, For example, kinematic data generated during a particular portion of a surgical session may indicate movement of a surgical instrument from a first position within the surgical area to a second position within the surgical area. Based on this kinematic data, system 100 may determine that an event (i.e., movement of the surgical instrument located within the surgical area) is occurring or has occurred.

As another example, image data (e.g., a visible light image stream) may indicate that a particular surgical instrument has remained out of a field of view of an imaging device for a predetermined period of time. Such image data may be indicative of an idle state event.

As a further example, surgical instrument data generated during a particular portion of a surgical session may indicate energization of a cautery instrument. Such surgical instrument data may be indicative of an energization event, In some examples, event detection unit 812 may implement a machine learning model. System 100 may apply surgical session data 810 as inputs to the machine learning model, which may use surgical session data 810 to identify one or more unique patterns of surgical system operations and associate events with the detected patterns of surgical system operations.

In response to detection of a particular event that occurs within the surgical area, event detection unit 812 may output event data 814 representative of the detected event to display mode unit 802.

Display mode unit 802 may analyze the event data 814 and determine, based on the detected event, a display mode in which system 100 should operate. Display mode unit 802 may perform any suitable heuristic, process, and/or operation that may be performed or executed by system 100 and that may be configured determine a display mode based on event data 814. In some examples, display mode unit 802 may include or be implemented by hardware and/or software components (e.g., processors, memories, communication interfaces, instructions stored in memory for execution by the processors, etc.), such as storage facility 102 and/or processing facility 104 of system 100.

Display mode unit 802 may determine the display mode based on event data 814 in any suitable way. For example, FIG. 9 shows an exemplary display mode table 900 ("table 900") that may be maintained or otherwise accessed by system 100 in order to determine the display mode to which system 100 should switch. As shown in column 902, table 900 includes a plurality of entries representative of various events that may occur within a surgical area. As shown in column 904, table 900 specifies a display mode to which system 100 should switch in response to detection of the associated event.

Table 900 may also include additional parameters that may be used by system 100 to determine a display mode. For example, as shown in column 906, display mode table 900 may specify an instrument type for one or more event entries. Additionally, as shown in column 908, display mode table 900 may specify a current display mode (i.e., the display mode in which system 100 is operating when the event is detected) for one or more event entries. Additionally, as shown in column 910, display mode table 900 may specify a User ID for one or more event entries. By associating the display mode with multiple different parameters, table 900 may determine the appropriate display mode based on the context of the surgical session.

To illustrate, table 900 indicates that, in response to detection of an "energization" event, the display mode is to be switched to a "visible_light" display mode. As another example, table 900 indicates that, in response to detection of a "movement" event of a "graspers" instrument, the display mode is to be switched to an "augmented" display mode. However, in response to detection of a "movement" event of a "cautery_hook" instrument, the display mode is to be switched to a "visible_light" display mode. As another example, table 900 indicates that, in response to detection of an "idle-state" event occurring while system 100 operates in a "visible_light" display mode, the display mode is to be switched to an "augmented" display mode. However, in response to detection of an "idle-state" event occurring while system 100 operates in an "augmented" display mode, the display mode is to be switched to a "fluorescence" display mode. As a further example, in response to detection of an "operation" event that occurs while system 100 operates in a "fluorescence" display mode, the display mode is to be switched to a "visible_light" display mode if "user_A" is logged-in to system 100 and is to be switched to an "augmented" display mode if "user_B" is logged-in to system 100.

It will be recognized that table 900 is not limited to the parameters shown in FIG. 9, and may include any set of parameters as may suit a particular implementation.

Referring again to FIG. 8, once display mode unit 802 has determined the display mode based on event data 814, display mode unit 802 may switch from operating in the first display mode to operating in a second display mode. To this end, while system 100 is operating in the second display mode, display mode unit 802 may generate a second video stream based on a second set of at least one of visible light image stream 804 and fluorescence image stream 806. For example, when the second display mode is a visible light display mode the second video stream is based only on visible light image stream 804. When the second display mode is an augmented display mode the second video stream is an augmented stream based on a combination of visible light image stream 804 and fluorescence image stream 806. When the second display mode is a fluorescence display mode the second video stream is based only on fluorescence image stream 808.

After generation of the second video stream, display mode unit 802 may output, to the display device while system 100 is operating in the second display mode, the second video stream as output video stream 808.

In some examples, system 100 may disable a surgical instrument functionality (e.g., a tissue interaction functionality, a sensing functionality, a movement functionality, etc.) of a surgical instrument located within the surgical area while system 100 is operating in the second display mode. For example, when the second display mode is a fluorescence display mode a surgeon may be unable to see surgical instruments located within the surgical area (see FIG. 6) because fluorescence illumination may not be emitted from the surgical instruments. when system 100 switches to operating in a fluorescence display mode system 100 may disable, for the duration of the fluorescence display mode, a tissue interaction functionality (e.g., energization of a cautery instrument, operation of a needle driver, operation of scissors, etc.) of a surgical instrument located within the surgical area. When system 100 switches to a different display mode (e.g., a visible light display mode or an augmented display mode), system 100 may enable the surgical instrument functionality.

Figure 10:
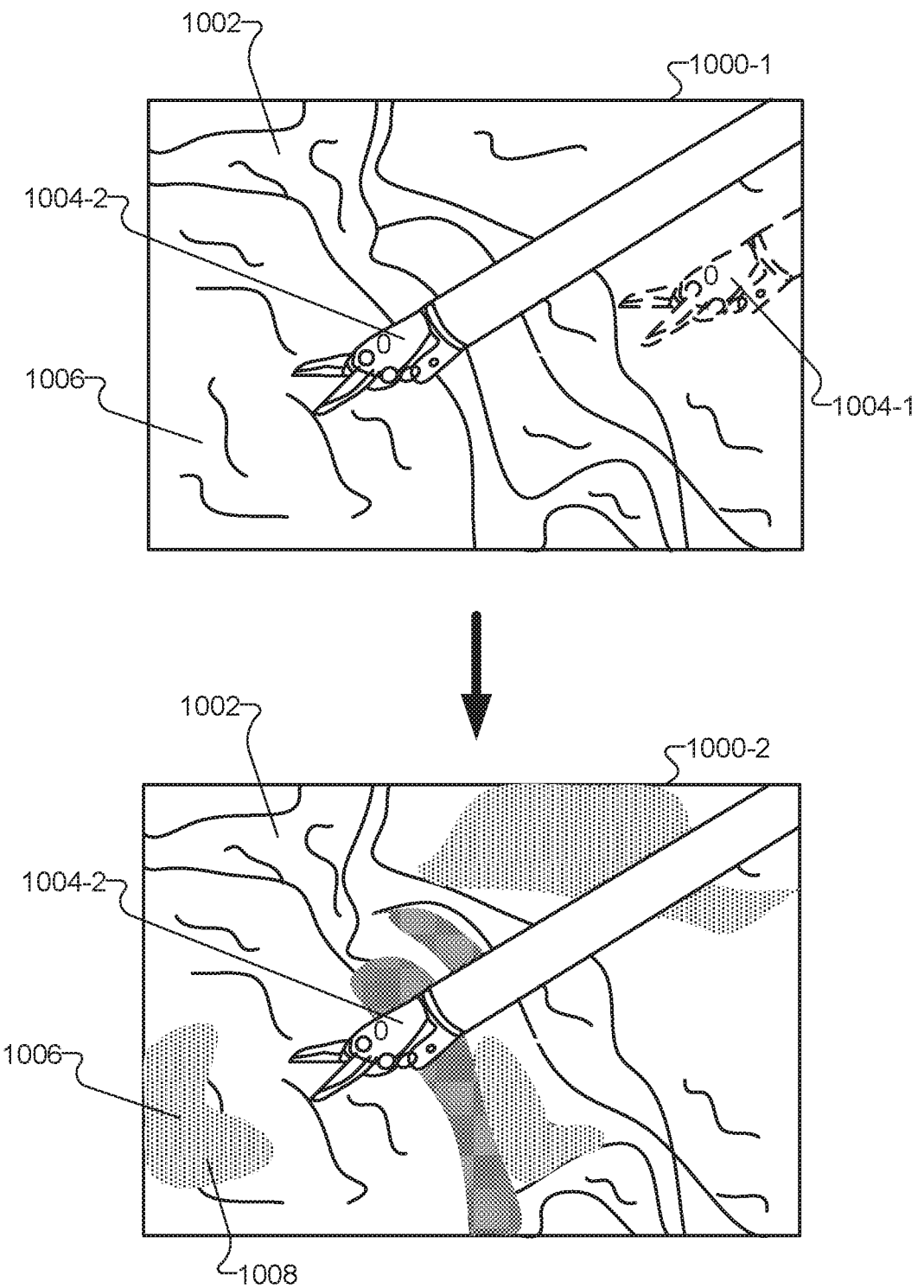
FIG. 10 illustrates an exemplary switching of a display mode in response to detection of an event that occurs within a surgical area according to principles described herein.

An exemplary operation of system 100 will now be described with reference to FIG. 10. FIG. 10 illustrates an exemplary image 1000-1 of a surgical area, as captured by an imaging device (e.g., imaging device 302) and displayed by a display device (e.g., stereo viewer 204 of surgical system 200) in a visible light display mode. As shown, image 1000-1 depicts a portion of tissue 1002 and a surgical instrument 1004 that are within the field of view of the imaging device. While system 100 is operating in a visible light display mode, surgical instrument 1004 is moved from a first position (indicated by 1004-1) to a second position (indicated by 1004-2) located within a predetermined distance (e.g., 10 mm) of anatomical feature 1006 (e.g., a ureter, a blood vessel, etc.).

System 100 may detect that surgical instrument 1004 (1004-2) is located within a predetermined distance of anatomical feature 1006 and, in response, automatically switch from operating in the visible light display mode to operating in an augmented display mode. FIG. 10 illustrates an exemplary image 1000-2 of the surgical area, as captured by the imaging device and displayed by the display device in the augmented display mode. As shown, image 1000-2 depicts tissue 1002 and surgical instrument 1004 in normal visible light, and further depicts fluorescence region 1008 superimposed on anatomical feature 1006 to thereby highlight anatomical feature 1006.

By switching to a display mode based on a fluorescence image stream when a surgical instrument gets close to a particular anatomical feature, a surgeon can be alerted of the presence and location of the particular anatomical and avoid unintended injury to the anatomical feature.

System 100 may detect that a surgical instrument is located within a predetermined distance of an anatomical feature in any suitable way. The position of a surgical instrument relative to an anatomical feature may be determined based on any suitable surgical session data, such as kinematic data associated with the surgical instrument, image data (e.g., a visible light image stream and/or a fluorescence image stream), and/or depth data of the surgical area. Various operations that may be performed by system 100 to determine that a surgical instrument is located within a predetermined distance of an anatomical feature will now be described.

System 100 may identify an anatomical feature located within the surgical area. In some examples, system 100 may identify an anatomical feature based on fluorescence illumination emitted from the surgical area, For example, the concentration of a fluorescence imaging agent may be higher in a particular anatomical feature than in tissue surrounding the anatomical feature, Accordingly, system 100 may determine that an illumination intensity of fluorescence illumination emitted from the surgical area exceeds a predetermined value at a particular region of the surgical area and identify the particular region of the surgical area as the anatomical feature.

In additional or alternative examples for identifying an anatomical feature, system 100 may apply a feature detection heuristic to one or more images of the surgical area (e.g., a visible light image stream 804 and/or a fluorescence image stream 806), The feature detection heuristic may be configured to identify the anatomical feature in the image(s) of the surgical area. For example, the feature detection heuristic may perform image recognition and/or pattern recognition on the image(s) of the surgical area.

Once system 100 has identified the particular anatomical feature, system 100 may determine a position of the anatomical feature in the surgical area. In some examples, system 100 may determine the position of the anatomical feature based on the visible light image stream and/or the fluorescence image stream, For example, system 100 may access or generate depth data based on the visible light image stream and/or the fluorescence image stream and determine the position of the anatomical feature based on the depth data.

System 100 may determine a current position of the surgical instrument based on the visible light image stream and/or kinematic data associated with the surgical instrument. For example, system 100 may access or generate depth data based on the visible light image stream and determine the position of the anatomical feature based on the depth data and/or the kinematic data.

Once system 100 has determined the positions of the anatomical feature and the surgical instrument, system 100 may determine that a difference between the position of the anatomical feature and the current position of the surgical instrument is less than the predetermined distance. The value of the predetermined distance may be any value as may suit a particular implementation (e.g., 1 mm, 5 mm, 7 mm, etc.). In some examples, the value of the predetermined distance may depend on the type of surgical instrument, such as 5 mm for a cautery instrument, 7 mm for a cutting instrument, and 1 mm for a grasping instrument. Additionally or alternatively, the value of the predetermined distance may be specified by user input.

In response to determining that the position of the anatomical feature and the current position of the surgical instrument is less than the predetermined distance, system 100 may switch from operating in the first display mode to operating in the second display mode.

In some examples, the anatomical feature may be a known anatomical feature to be monitored during a surgical session. For example, during a hysterectomy a ureter may be positioned close to a working area in the surgical area (e.g., behind fascia tissue). Accordingly, system 100 may switch to operating in the second display mode only when a surgical instrument is within a predetermined distance of a particular anatomical feature. The particular anatomical feature may be specified by user input or based on the type of surgical procedure being performed.

In alternative examples, the anatomical feature may be any anatomical feature having a fluorescence illumination intensity that exceeds a predetermined intensity value. Accordingly, system 100 may alert a surgeon when a surgical instrument moves near any anatomical feature from which fluorescence illumination is emitted.

Referring again to FIG. 10, system 100 may detect, while operating in the augmented display mode, an additional event that occurs within the surgical area. For example, if system 100 detects an idle state event associated with surgical instrument 1004 (e.g., surgical instrument 1004 has not moved or been operated for a predetermined period of time, such as 20 seconds), system 100 may switch from operating in the augmented display mode to operating in a fluorescence display mode (such as shown in FIG. 6). On the other hand, if system 100 detects operation of a tissue interaction functionality of surgical instrument 1004 (e.g., energization of surgical instrument 1004), system 100 may switch from operating in the augmented display mode to operating in the visible light mode by displaying image 1000-1 (as shown in FIG. 10).

Figure 11:
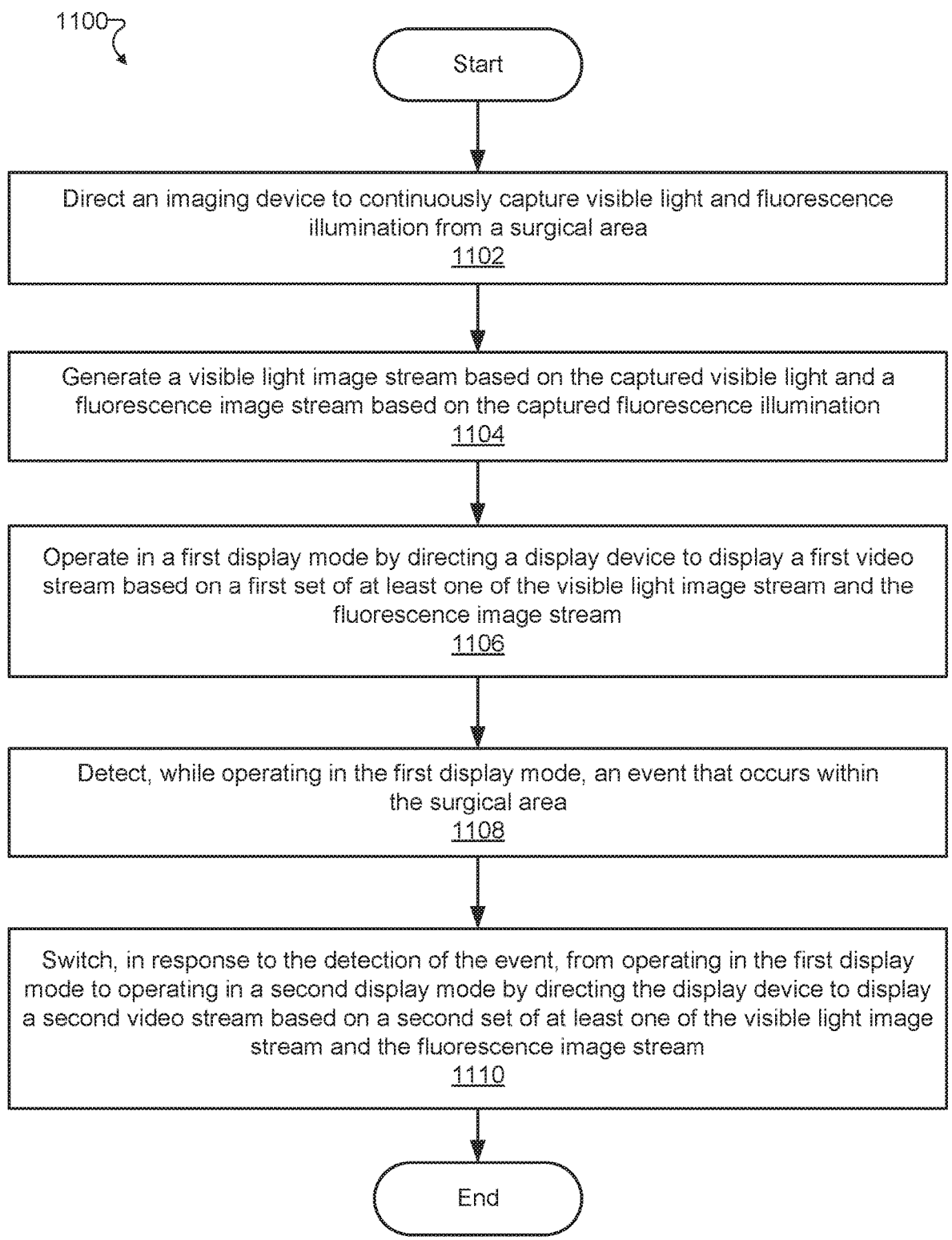
FIG. 11 shows an exemplary display mode switching method according to principles described herein.

FIG. 11 shows an exemplary display mode switching method 1100. While FIG. 11 illustrates exemplary operations according to one embodiment, other embodiments may omit, add to, reorder, combine, and/or modify any of the steps shown in FIG. 11 One or more of the operations shown in in FIG. 11 may be performed by system 100, any components included therein, and/or any implementation thereof.

In operation 1102, an augmented medical vision system directs an imaging device to continuously capture visible light from a surgical area and fluorescence illumination from the surgical area. Operation 1102 may be performed in any of the ways described herein.

In operation 1104, the augmented medical vision system generates a visible light image stream based on the captured visible light and a fluorescence image stream based on the captured fluorescence illumination. Operation 1104 may be performed in any of the ways described herein.

In operation 1106, the augmented medical vision system operates in a first display mode by directing a display device to display a first video stream based on a first set of at least one of the visible light image stream and the fluorescence image stream. Operation 1106 may be performed in any of the ways described herein.

In operation 1108, the augmented medical vision system detects, while operating in the first display mode, an event that occurs within the surgical area. Operation 1108 may be performed in any of the ways described herein.

In operation 1110, the augmented medical vision system switches, in response to the detection of the event, from operating in the first display mode to operating in a second display mode by directing the display device to display, in place of the first video stream, a second video stream based on a second set of at least one of the visible light image stream and the fluorescence image stream, the first set being different than the second set. Operation 1110 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 12:
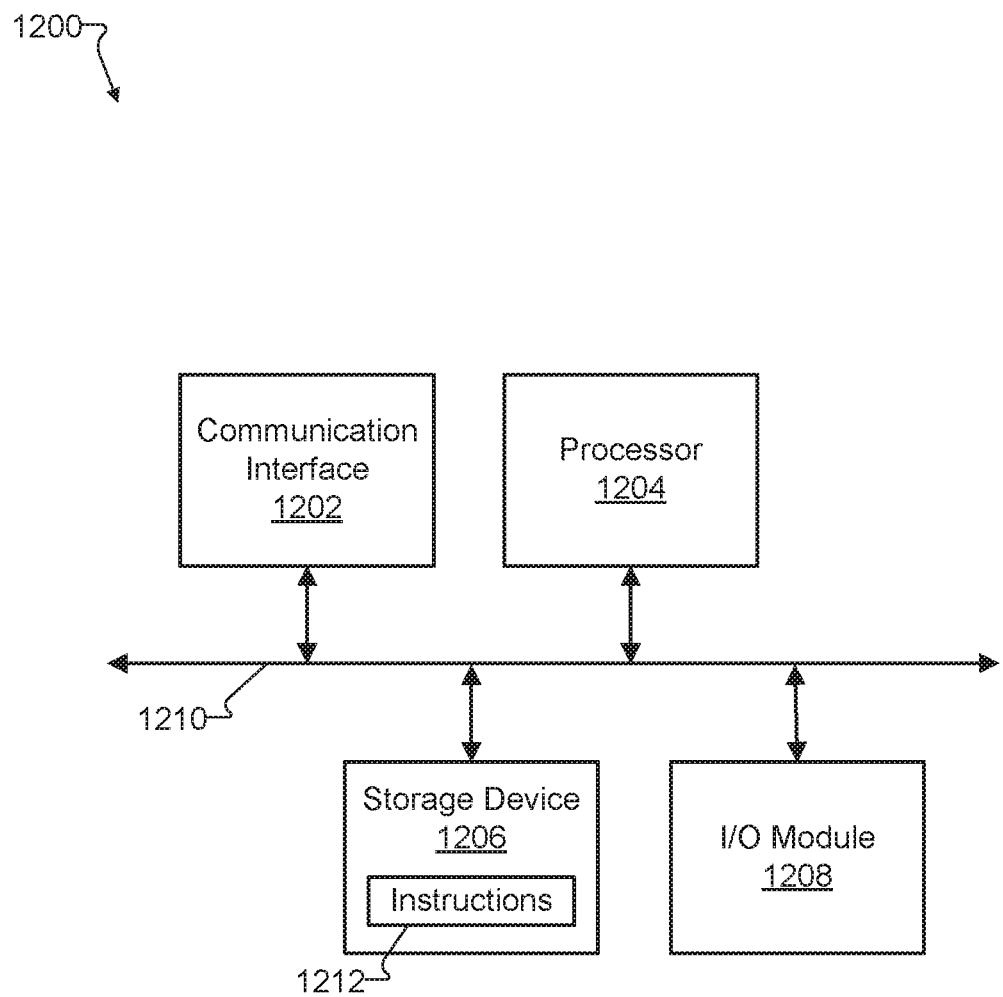
FIG. 12 illustrates an exemplary computing device according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1200. For example, processing facility 104 may be implemented by processor 1204 and storage facility 102 may be implemented by storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
generate a visible light image stream based on visible light from a surgical area captured by an imaging device and generate a fluorescence image stream based on fluorescence illumination from the surgical area captured by the imaging device,
operate in a first display mode by directing a display device to display a first video stream based on a first set of at least one of the visible light image stream and the fluorescence image stream,
determine, while operating in the first display mode, that an event occurs within the surgical area, the event comprising at least one of a fluorescence event or an operation of a surgical instrument other than the imaging device,
switch, in response to the determining that the event occurs within the surgical area, from operating in the first display mode to operating in a second display mode,
determine, while operating in the second display mode, that an additional event occurs within the surgical area, and
switch, in response to the determining that the additional event occurs within the surgical area, from operating in the second display mode to operating in a third display mode,
wherein the operating in the second display mode comprises directing the display device to display, in place of the first video stream, a second video stream based on a second set of at least one of the visible light image stream and the fluorescence image stream, the first set being different than the second set, and
wherein the operating in the third display mode comprises directing the display device to display, in place of the second video stream, a third video stream based on a third set of at least one of the visible light image stream and the fluorescence image stream, the third set being different than the first set and the second set.

2. The system of claim 1, wherein:
the event comprises the operation of the surgical instrument;
the processor is further configured to execute the instructions to access kinematic data associated with the surgical instrument; and
the determining that the event occurs within the surgical area is based on the kinematic data.

3. The system of claim 1, wherein the event comprises the operation of the surgical instrument and the determining that the event occurs within the surgical area comprises detecting an operation of a tissue interaction functionality of the surgical instrument.

4. The system of claim 1, wherein the event comprises the operation of the surgical instrument and the determining that the event occurs within the surgical area comprises detecting a movement of the surgical instrument to a position located within a predetermined distance of an anatomical feature located within the surgical area.

5. The system of claim 4, wherein the detecting of the movement of the surgical instrument to the position located within the predetermined distance of the anatomical feature comprises:
identifying the anatomical feature based on the fluorescence illumination,
determining a position of the anatomical feature based on at least one of the visible light image stream and the fluorescence image stream,
determining a current position of the surgical instrument based on at least one of the visible light image stream and kinematic data associated with the surgical instrument, and
determining that a difference between the position of the anatomical feature and the current position of the surgical instrument is less than the predetermined distance.

6. The system of claim 5, wherein the identifying of the anatomical feature comprises:
determining that an intensity of the fluorescence illumination exceeds a predetermined value at a particular region of the surgical area, and
identifying the particular region of the surgical area as the anatomical feature.

7. The system of claim 5, wherein the identifying of the anatomical feature comprises applying a feature detection heuristic to at least one of the visible light image stream and the fluorescence image stream.

8. The system of claim 1, wherein:
the event comprises the fluorescence event,
the processor is further configured to execute the instructions to determine an intensity of the fluorescence illumination, and
the determining that the event occurs within the surgical area comprises detecting that the intensity of the fluorescence illumination has reached a predetermined value.

9. The system of claim 1, wherein the processor is further configured to execute the instructions to:
- determine, while operating in the second display mode, that an additional event occurs within the surgical area, and
- switch, in response to the determining that the additional event occurs within the surgical area, from operating in the second display mode to operating in the first display mode.

10. A system comprising:
a memory storing instructions; and
a processor communicatively coupled to the memory and configured to execute the instructions to:
- generate a visible light image stream based on visible light from a surgical area captured by an imaging device and generate a fluorescence image stream based on fluorescence illumination from the surgical area captured by the imaging device,
- operate in a first display mode by directing a display device to display a first video stream based on a first set of at least one of the visible light image stream and the fluorescence image stream,
- determine, while operating in the first display mode, that an event occurs within the surgical area, the event comprising at least one of a fluorescence event or an operation of a surgical instrument other than the imaging device,
- switch, in response to the determining that the event occurs within the surgical area, from operating in the first display mode to operating in a second display mode, and
- disable a surgical instrument functionality of a surgical instrument located within the surgical area while operating in the second display mode,
- wherein the operating in the second display mode comprises directing the display device to display, in place of the first video stream, a second video stream based on a second set of at least one of the visible light image stream and the fluorescence image stream, the first set being different than the second set and the second set including the fluorescence image stream.

11. The system of claim 10, wherein
the surgical instrument comprises a cautery instrument, and
the surgical instrument functionality comprises energization of the cautery instrument.

12. The system of claim 1, wherein
the first set includes only the visible light image stream, and
the second set includes only the fluorescence image stream or a combination of the visible light image stream and the fluorescence image stream.

13. The system of claim 1, wherein
the first set includes only the fluorescence image stream, and
the second set includes only the visible light image stream or a combination of the visible light image stream and the fluorescence image stream.

14. The system of claim 1, wherein
the first set includes a combination of the visible light image stream and the fluorescence image stream, and
the second set includes only the visible light image stream or only the fluorescence image stream.

15. A system comprising:
a memory storing instructions; and
a processor communicatively coupled to the memory and configured to execute the instructions to:
- generate a visible light image stream based on visible light from a surgical area captured by an imaging device and generate a fluorescence image stream based on fluorescence illumination from the surgical area captured by the imaging device,
- direct a display device to display only the visible light image stream,
- determine, while the visible light image stream is displayed, that an event occurs within the surgical area, the event comprising at least one of a fluorescence event or an operation of a surgical instrument other than the imaging device, and
- switch, in response to the determining that the event occurs within the surgical area, from directing the display device to display only the visible light image stream to directing the display device to display a second video stream based at least in part on the fluorescence image stream,
- determine, while the display device displays the second video stream, that an additional event occurs within the surgical area, and
- switch, in response to the determining that the additional event occurs with in the surgical area, from directing the display device to display the second video stream to directing the display device to display a third video stream based at least in part on the fluorescence image stream, wherein the third video stream is different than the second video stream.

16. A method comprising:
generating, by an augmented medical vision system, a visible light image stream based on visible light from a surgical area captured by an imaging device and generate a non-visible light image stream based on non-visible light from the surgical area captured by the imaging device;
operating, by the augmented medical vision system, in a first display mode by directing a display device communicatively coupled with the augmented medical vision system to display a first video stream based on a first set of at least one of the visible light image stream and the non-visible light image stream;
determining, by the augmented medical vision system while operating in the first display mode, that an event occurs within the surgical area, the event comprising at least one of a fluorescence event or an operation of a surgical instrument other than the imaging device;
switching, by the augmented medical vision system in response to the determining that the event occurs within the surgical area, from operating in the first display mode to operating in a second display mode;
determining, by the augmented medical vision system while operating in the second display mode, that an additional event occurs within the surgical area; and
switching, by the augmented medical vision system in response to the determining that the additional event occurs within the surgical area, from operating in the second display mode to operating in the first display mode or a third display mode,
wherein the operating in the second display mode comprises directing the display device to display, in place of the first video stream, a second video stream based on a second set of at least one of the visible light image stream and the non-visible light image stream, the first set being different than the second set; and
wherein the operating in the third display mode comprises directing the display device to display, in place of the second video stream, a third video stream based on a third set of at least one of the visible light image stream and the non-visible light image stream, the third set being different than the first set and the second set.

17. The method of claim 16, wherein the event comprises the operation of the surgical instrument and the determining that the event occurs within the surgical area comprises detecting an operation of a tissue interaction functionality of the surgical instrument or detecting a movement of the surgical instrument to a position located within a predetermined distance of an anatomical feature located within the surgical area.

18. The method of claim 16, further comprising:
determining an intensity of the non-visible light, the non-visible light comprising fluorescence illumination, wherein the event comprises the fluorescence event and the determining that the event occurs within the surgical area comprises detecting that the intensity of the fluorescence illumination has reached a predetermined value.

* * * * *